US006733287B2

(12) United States Patent
Wilkerson (10) Patent No.: US 6,733,287 B2
(45) Date of Patent: May 11, 2004

(54) MOLAR TUBE LOCK

(76) Inventor: Michael K. Wilkerson, 4910 Kingsboro Ct., Midland, TX (US) 79705

( * ) Notice: Subject to any disclaimer, the term of this patent is extended or adjusted under 35 U.S.C. 154(b) by 120 days.

(21) Appl. No.: 10/091,089

(22) Filed: Mar. 6, 2002

(65) Prior Publication Data

US 2003/0170585 A1 Sep. 11, 2003

(51) Int. Cl.[7] .................................................. A61C 3/00
(52) U.S. Cl. ........................................... 433/17; 433/13
(58) Field of Search ............................ 433/8, 9, 10, 11, 433/12, 13, 14, 15, 16, 17, 18, 19, 20, 21, 22, 23, 24

(56) References Cited

U.S. PATENT DOCUMENTS

| 2,046,414 | A | * | 7/1936 | Russell | 433/17 |
|---|---|---|---|---|---|
| 3,238,619 | A | * | 3/1966 | Brunson et al. | 433/13 |
| 3,486,231 | A | * | 12/1969 | Nelson | 433/17 |
| 3,597,845 | A | * | 8/1971 | Russ | 433/17 |
| 4,355,975 | A | | 10/1982 | Fujita | 433/11 |
| 4,424,032 | A | | 1/1984 | Howe | 433/19 |
| 4,781,582 | A | * | 11/1988 | Kesling | 433/17 |
| 4,988,292 | A | | 1/1991 | Rosen | 433/8 |
| 5,057,012 | A | | 10/1991 | Kesling | 433/17 |
| 5,071,345 | A | | 12/1991 | Rosen | 433/17 |
| 5,681,164 | A | | 10/1997 | Bass | 433/6 |
| 5,727,941 | A | | 3/1998 | Kesling | 433/17 |
| 6,036,488 | A | | 3/2000 | Williams | 433/19 |
| 6,217,323 | B1 | | 4/2001 | Liou | 433/18 |

* cited by examiner

*Primary Examiner*—John J. Wilson
(74) *Attorney, Agent, or Firm*—Christopher J. Whewell; Western Patent Group (57) ABSTRACT

A molar tube having a first face portion that is adapted to be adhered to a molar tooth, a second face portion, and a mesial-distal length dimension. There is a body portion disposed on the second face portion of the base portion, and the body portion comprises an upper portion and a lower portion. The body portion further comprises a lumen that is adapted to receive an archwire, wherein the lumen has an axis which substantially coincides with the mesial-distal length dimension of the base portion. The body portion further comprises a boss comprising a threaded bore that is adapted to receive a setscrew, wherein the threaded bore has an axis. The axis of the threaded bore intersects with the mesial-distal length dimension to form an angle of any degree between 15 degrees and 175 degrees, including every degree therebetween. A molar tube according to the invention allows for easy adjustment of the tension in an archwire used in an orthodontic dental treatment, and provides for the painless withdrawal of the archwire at any time during or following the treatment.

20 Claims, 8 Drawing Sheets

MOLAR TUBE LOCK

The present invention relates generally to a molar tube, and more particularly to a molar tube that is adapted to receive an archwire. More particularly still, the invention relates to a molar tube that facilitates the withdrawal or adjustment of an archwire after the archwire has been employed in an orthodontic treatment. The invention allows an archwire to be locked in the molar tube, thus preventing slippage.

BACKGROUND

During orthodontic treatment and the use of fixed appliances on the teeth, including brackets for receiving an archwire, molar tubes are employed to anchor the distal ends of the archwire. The molar tubes are mounted on molar teeth, which constitute the posterior teeth in the mouth. Following the placement of the distal ends of the archwire in molar tubes, it is customary to trim the ends of the wire and then bend the ends that protrude from the distal ends of the tubes to prevent the archwire from moving mesially through the tubes which could result in spaces opening mesial to the anchor molars. The archwire is otherwise secured to brackets on the adjacent posterior and anterior teeth, and therefore it is important not to allow mesial movement of the archwire when the fixed appliances are in place. Additionally, in prior art methods, the distal ends of the archwire are bent in a direction to prevent the ends from striking/irritating the patient's hard or soft tissues, the hard tissues being the enamel surfaces of the teeth, and the soft tissues being the gingiva or cheek.

During the course of treatment using molar tubes of the prior art, it is often necessary to remove and replace the archwires with the bent ends. Such a procedure requires straightening the bent ends as much as possible and then pulling those bent ends mesially through the molar tubes. Inasmuch as it is difficult, if not impossible, to completely straighten the ends of the wires, considerable forces are required to withdraw or pull the wires through the tubes. High amounts of force are first required to deflect the end of the wire so it can pass through the tube and second to overcome the friction created by drawing the deformed wire through the length of the tube. This is particularly the case where full size rectangular archwires are employed to fit rectangular tubes, wherein the tolerances are +−0.0.001 inch (0.025 mm). The application of the necessary forces to remove archwires having bent ends is often quite discomforting to the patient. It not only is discomforting by the force required but also because of the duration of that force as the archwire is pulled through the entire length of the tube. The well-being and comfort of a patient is particularly important as it can relate to the results achieved during orthodontic treatment.

Heretofore, there have been molar tubes for receiving archwires and having flared openings at the mesial end to facilitate the threading of the archwire into the tube, such as shown in U.S. Pat. No. 5,556,277. There have also been a number of molar tubes for lip bumpers and head gear having the inlet mesial end enlarged to facilitate the mounting of a lip bumper or head gear, such as shown in U.S. Pat. Nos. 3,815,238; 4,963,092; 5,057,012; 5,151,028; and 5,292,248. It is also known to provide a bracket that permits limited tipping relative to the archwire, as disclosed in U.S. Pat. Nos. 4,842,512; 4,859,179, and 4,877,398.

U.S. Pat. No. 4,355,975 teaches an orthodontic appliance that comprises a plate bonded to a tooth. The plate is connected to the main body of the bracket. The covering orthodontic cap for fixing the wire is connected to the main body of the bracket. The cap can be removed from the bracket since it is fixed and connected thereto with a connecting part and elastic connecting device. The bracket or the cap is provided with a shearing groove that prevents the caps from sliding off and provides for locking and removal of the cap by simple operations.

U.S. Pat. No. 4,424,032 discloses an orthodontic jaw correction appliance comprising a positioning means operatively disposed between the upper and lower dental arches. The positioning means includes a pair of cooperatively engaged elements, one of which is associated with one arch and the other of which is associated with the other arch. The elements are operable as the jaw closes to translate the natural jaw closure force into a corrective force component acting between the two arches. The improvement for operatively relating one element to its associated arch comprises a generally U-shaped splint comprising a generally U-shaped molded plastic body conforming to the general U-shape of the associated arch for application to the cusps of teeth thereof including molar teeth on laterally opposite sides and all teeth mesial to the molar teeth. There is bonding means disposed on the U-shaped molded plastic body for bonding the molded plastic body to the cusps of the teeth so that the splint acts through the bonding means stabilizes the molar teeth and all teeth mesial thereto as a unit to effect jaw correction. The one element and the splint have a point of operative coupling which is mesial to the point of bonding of the splint to at least some of the molar teeth.

U.S. Pat. No. 4,988,292 sets forth an abutment for an orthodontic anchorage that is mountable on an osseointegrated dental implant fixture in the same manner as are components which are used to support prosthodontic restorations. The abutment of the invention is adjustable around the axis of the implant fixture, and it supports a mount for holding an orthodontic anchor fixed to a buccal or a lingual side of the abutment. The mount is adjustable around an axis running between the buccal and lingual surfaces.

U.S. Pat. No. 5,057,012 describes a molar tube for a lip bumper or a face bow comprising: 1) a base having a lingually-facing attaching surface for attaching to a tooth; 2) an elongated, mesioldistally-extending tubular body projecting buccally from the base, wherein the body includes an opening therethrough for receiving the distal ends of a lip bumper or a face bow, and having an inside lingual wall and an outside buccal wall. The opening is flared from the distal end to the mesial end such that the mesial end is larger than the distal end, and of a size substantially larger than the distal end of a lip bumper or a face bow. The distal end of the opening is round and sized to closely receive the distal end of the lip bumper or face bow to provide lateral control. The mesial end is oval and has a vertical dimension adapted to closely receive the distal end of the lip bumper or face bow to control tipping, and the long axis of the oval mesial end extends generally horizontally, whereby insertion of a distal end of a lip bumper or a face bow is greatly enhanced.

U.S. Pat. No. 5,071,345 teaches a prefabricated dental crown analog having an exterior size and contour to approximate the dimensions and shape of a natural tooth at the site, and an orthodontic wire anchor consisting essentially of hollow tubular means providing an integral passage extending mesially-distally through the analog closer to one of the exterior buccal or lingual surfaces than to the center thereof, for passage of an orthodontic wire through the passage whereby the wire may be anchored with the crown analog. The crown of the invention is intended for use in the mouth of a patient having an endosseous dental implant fixture or the like installed in the patient's jawbone at an edentulous site.

U.S. Pat. No. 5,681,164 discloses and orthopaedic modular assembly comprising: 1) a housing component of rigid material providing a first passage; 2) a second component in the form of a lingual pad support having a first arm adapted to form a snug sliding fit within the first housing passage; 3) a second arm extending at an angle to the first arm, and adapted to conform to the line of one side of a patient's mouth; and 4) a latch means associated with the housing component, whereby the first arm of the second component is held within the first passage of the housing component by the latch means and is slidably adjustable relative to the housing component to any one of a plurality of predetermined latched positions.

U.S. Pat. No. 5,727,941 provides an implant arrangement for securing a denture to a jawbone, the implant arrangement comprising: 1) an implant shaft means having a central axis, a first end for insertion into the jawbone and a second end; 2) a securing means including a threaded bore formed at the second end for securing the denture thereto, the threaded bore being inclined with a predetermined angle relative to the central axis; 3) an insertion tool means for inserting the implant shaft means into the jawbone, wherein the insertion tool means has a central axis and a first end removably connected to the implant shaft for rotationally inserting the implant shaft into the jawbone; and 4) a connection means formed at the first end of the insertion tool means with an inclination relative to the central axis of the insertion tool means corresponding to the predetermined angle, the connecting means removably interfacing the insertion tool means and the implant shaft, wherein the central axis of the insertion tool means is coaxial with the central axis of the implant shaft.

U.S. Pat. No. 6,036,488 shows a pivotal mounting boss assembly for attachment to an orthodontic band for the pivotal mounting boss of an arch expansion appliance comprising: 1) a base casing, including a base segment for attachment to the orthodontic band, the base segment having an opening formed therein, the opening disposed to attach an arch wire; 2) a body segment being narrower in at least one cross sectional dimension than the base segment, and the body segment having a threaded bore formed therein; and 3) a screw threadedly engaged in the threaded bore, the screw disposed to attach to an eyelet of an expansion appliance.

U.S. Pat. No. 6,217,323 teaches an orthodontic dental distractor for rapid orthodontic tooth movement into a fresh extraction socket. The device includes: 1) a screw bar and a screw nut fixedly engaged with one end of the screw bar; 2) a first joint engageable with one end of the screw bar next to the screw nut and a first hook engageable with a canine band mounted on a canine; and 3) a second joint that is engageable with another end of the screw bar and has a second hook engageable with a molar band mounted on a molar. By turning the screw nut, the screw bar will move the first joint towards the second joint, thus moving the canine rearward toward the molar.

Even where the bent end of an archwire used in conjunction with prior art molar tubes is attempted to be straightened in the mouth, it is virtually impossible to completely straighten the wire, and therefore withdrawal of such an archwire from a tube requires the application of some force to the tube on withdrawal. That force, as applied to the tooth, results in discomfort to the patient.

It is therefore an object of the present invention to provide a new and improved molar tube for archwires that significantly decreases or eliminates the required force when removing an archwire from the tube.

A further object of the present invention is to provide a new and improved molar tube for archwires that reduces the force needed to withdraw a bent archwire from the tube and permits free distal crown tipping of the tooth on which the tube is mounted, thereby favorably contributing to the results obtainable during treatment.

A further object of the present invention is to provide a molar tube for archwires that is patient-friendly to reduce the forces required to withdraw a bent archwire from the tube during visits with the orthodontist, thereby reducing patient discomfort.

A further object of the invention is to allow an archwire to be secured to the molar teeth to provide superior anchorage over cinching the distal ends of the arch wire, i.e., so as to not allow molar teeth to drift forward if so desired. A molar tube lock according to the invention acts as a molar stop.

Another object of the invention is to provide an alternative means to achieve retraction and closure of spaces mesial to the molar teeth. With a properly designed archwire and appropriate loops, the molar stop can secure an activated archwire to close spaces, essentially working similar to a tie back with ligature wire.

Another object of the invention is to prevent the need for omega loops and other such bends designed as molar stops, to prevent mesial movement of the molar teeth.

Another object of the invention is to enable archwire to be secured to allow for advancement of anterior teeth by locking the archwire to the molar tubes and allowing the archwire to extend slightly in front of anterior brackets, as in cases of class II, div. II diagnoses. Molar teeth, due to their size and anatomy are generally used for anchorage. Smaller teeth in front are moved essentially because the larger tooth is more positionally stable to applied forces. Loss of anchorage, or slippage of the molar teeth forward is desirable in some cases. Thus, a molar tube lock according to the invention would not be activated—to allow free movement of the archwire through the tube, i.e., molars move forward to close space versus anterior teeth moving backward to close the space. A molar tube lock according to the invention can be used afterwards, to prevent re-opening of spaces. Thus, the present invention is universal and can be used in all situations requiring advancement arches, retraction arches, reinforcement of molar anchorages, and prevention of spaces re-opening.

Another object is to provide a molar tube lock that allows the straight wire technique of orthodontic treatment to operate more efficiently.

Other objects, features and advantages of the invention will be apparent from the following detailed disclosure, taken in conjunction with the accompanying sheets of drawings, wherein like reference numerals refer to like parts

SUMMARY OF THE INVENTION

The above-mentioned problem of patient discomfort is solved by the present invention wherein a molar tube according to the present invention eliminates the need to bend archwires, as is the case when using molar tubes of the prior art, and thus inherently eliminates the use of force otherwise needed to mesially withdraw a bent archwire from the tube.

More particularly, a molar tube according to the present invention includes a lumen and a threaded boss comprising a threaded hole, wherein the axis of the threaded hole in the boss is disposed at an angle of approximately 45° to the axis of the lumen. Such an arrangement allows for the selective securing of an archwire at a desired position/tension within the lumen, while providing control over labiolingual and occlusogingival archwire movement for either round and rectangular archwires, and also torque control for rectangular archwires. Under such an arrangement, the force required to mesially withdraw a bent archwire through the tube is dramatically reduced, if not wholly eliminated in most cases.

The amount of initial force to draw the bent end of an archwire into the molar tube of the present invention and the subsequent force thereafter required to pull the archwire the full length of the tube and remove it from the tube may be reduced to a level of about 0 to 5 percent of what would normally be required with a conventional molar tube. This force reduction translates into enhanced patient comfort.

In its simplest form, a molar tube according to the present invention comprises a base portion having a first face portion that is adapted to be adhered to a molar tooth, a second face portion, and a mesial-distal length dimension. There is a body portion disposed on the second face portion of the base portion, and the body portion comprises an upper portion and a lower portion. The body portion further comprises a lumen that is adapted to receive an archwire, wherein the lumen has an axis which substantially coincides with the mesial-distal length dimension of the base portion. The body portion further comprises a boss comprising a threaded bore that is adapted to receive a setscrew, wherein the threaded bore has an axis. The axis of the threaded bore intersects with the mesial-distal length dimension to form an angle of any degree between 15 degrees and 175 degrees, including every degree therebetween.

DETAILED DESCRIPTION

Figure 1:
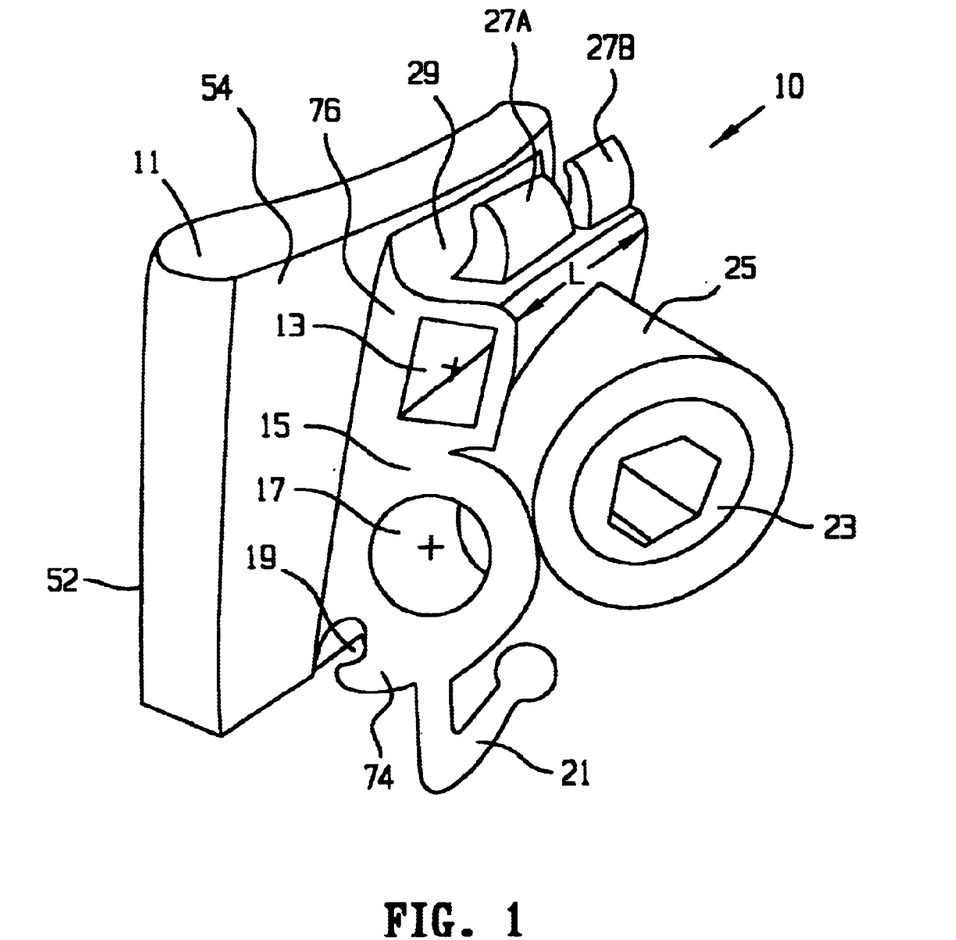
FIG. 1 is a perspective view of a molar tube according to the invention.

Referring to the drawings and initially to FIG. 1, there is shown a molar tube 10 according to the present invention. Such molar tube comprises a base portion 11 having a first face portion 52 and a second face portion 54. The base portion 11 is preferably fabricated according to an orthodontic prescription to deliver the correct tip and tongue features when it is subsequently properly secured to the tooth. The first face portion 52 is that surface which may to be bonded to the buccal side face of a molar tooth, using conventional dental bonding materials and methods known in the art as useful for bonding molar tubes to teeth. Typically, the face portion 52 is welded or soldered to a band that is then cemented to the molar teeth, as is known in the art; however, direct bonding is also acceptable. Disposed on the second face portion 54 is a body portion 15 that incorporates the essential features of the invention.

One essential feature of the invention is a lumen 17 that is adapted to receive an archwire that is circular in cross-section. Such lumen 17 is located within and passes completely through the entire body portion 15 in a mesial-distal direction.

According to a preferred form of the invention, there is a second lumen 13 that is adapted to receive an archwire which is square or rectangular in cross-section. Such lumen 13 is located within and passes completely through the entire body portion 15 in a mesial-distal direction.

According to one preferred form of the invention, the lumens 13 and 17 are disposed within the body portion 15 and have axes that are parallel to one another, that is, the axis of lumen 13 is parallel to the axis of lumen 17. However, parallelism of the axes of the lumens is not completely essential, as the axes of these lumens with respect to one another may be inclined any amount between about 0 and 15 degrees without departing from the scope of the invention. The axes of the lumens 13 and 17 are disposed along the center of the lumen in each case. The dimension of the body portion 15 in the mesial-distal direction determines the length of the lumen in each case. Thus, that portion of each of the axes of the lumens 13 and 17 which is contained within the body portion 15 is a finite segment of the axis, which may conveniently be referred to in each case as the "contained axis" for a particular lumen. While a preferred form of the invention comprises a pair of lumens as described above, one having a circular or elliptical cross-section and the other having a square or rectangular cross-section, the present invention includes those cases where the body portion 15 only includes a single lumen, having either a circular, elliptical, rectangular, or square cross-section.

The body portion 15 also includes a boss portion 25 having a threaded bore (33, FIG. 2) comprising an axis through its centerline disposed therethrough. The threaded bore 33 is adapted to receive a setscrew 23 having threads on its external surface that are complementary to the threads in the inner portion of the threaded bore 33. The axis of the threaded bore within the boss portion 25 is disposed to be skew (not parallel, but never intersecting) to the axis of a lumen such as 13 or 17. For embodiments when both lumens 13 and 17 are present, it is most preferred that the axis of the threaded bore within the boss portion 25 is skew to both the contained axes of the lumens, and the axis of the threaded bore within the boss portion 25 passes between both the axes of the lumens 13 and 17. Such an arrangement is particularly beneficial, for cases within the scope of the invention wherein the distance between the centerlines of the lumens 13 and 17 is less is sufficient to enable a securing contact between the end of the set screw (71 in FIG. 2) to contact an archwire disposed with a lumen 13 or 17 when the set screw is threaded into the threaded bore of the body portion and tightened.

The body portion also includes a channel 19 at its lower portion along its mesial-distal direction to which other wares (such as elastics, ligature wires, etc.) known useful in orthodontics may be secured. There are also ears 27a and 27b that are curvedly contoured to function in cooperation with the upper portion 76 of the body 15 to define a channel 29 having a semi-circular cross-section to which other wares (such as elastics, ligature wires, etc.) known useful in orthodontics may be secured. This channel 29 has a length dimension L that coincides with the mesial-distal axis of the body portion 15 and base portion 11. According to a preferred form of the invention, the length dimension of the channel 19 coincides in length with the channel 29; however, channel 19 may be longer or shorter than channel 29, as dictated by the selection of the contours of the body portion 15. In a preferred form of the invention, there is also disposed at the lower portion 74 of the body portion 15 a hook arm 21, which is beneficial for securing elastics or other wares known useful in orthodontics to the molar tube of the invention.

Figure 2:
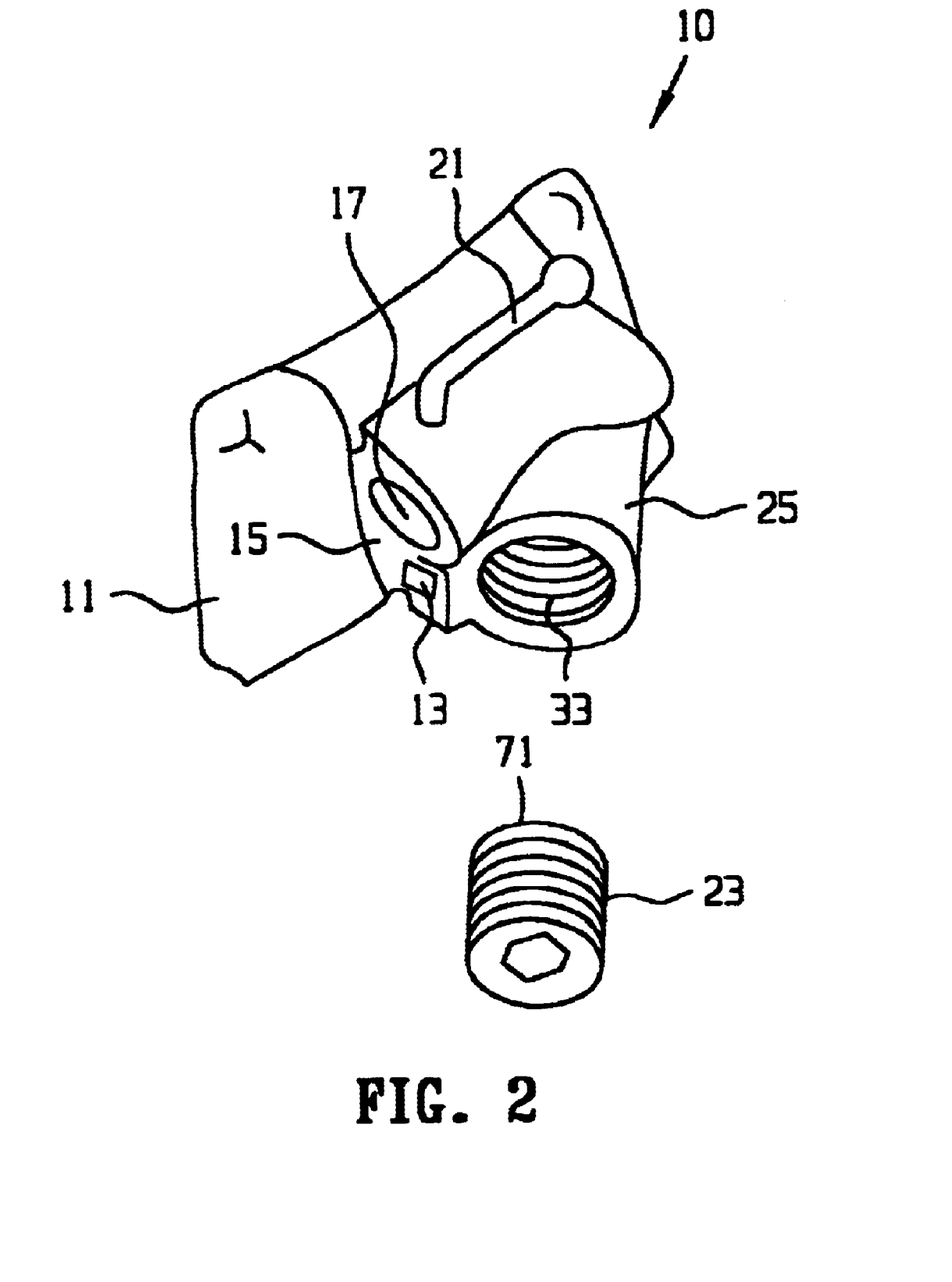
FIG. 2 is a perspective view of a molar tube according to the invention.

In FIG. 2 is shown a perspective view of molar tube 10 according to one form of the invention as in FIG. 1 that has been rotated 180 degrees. Here is shown the base portion 11, body portion 15, boss portion 25 having threaded bore 33 disposed therein, and hook arm 21. Also shown is the set screw 23 having an end portion 71 which, in use, securely contacts an archwire which is disposed in either of lumens 13, 17, or both.

Figure 3:
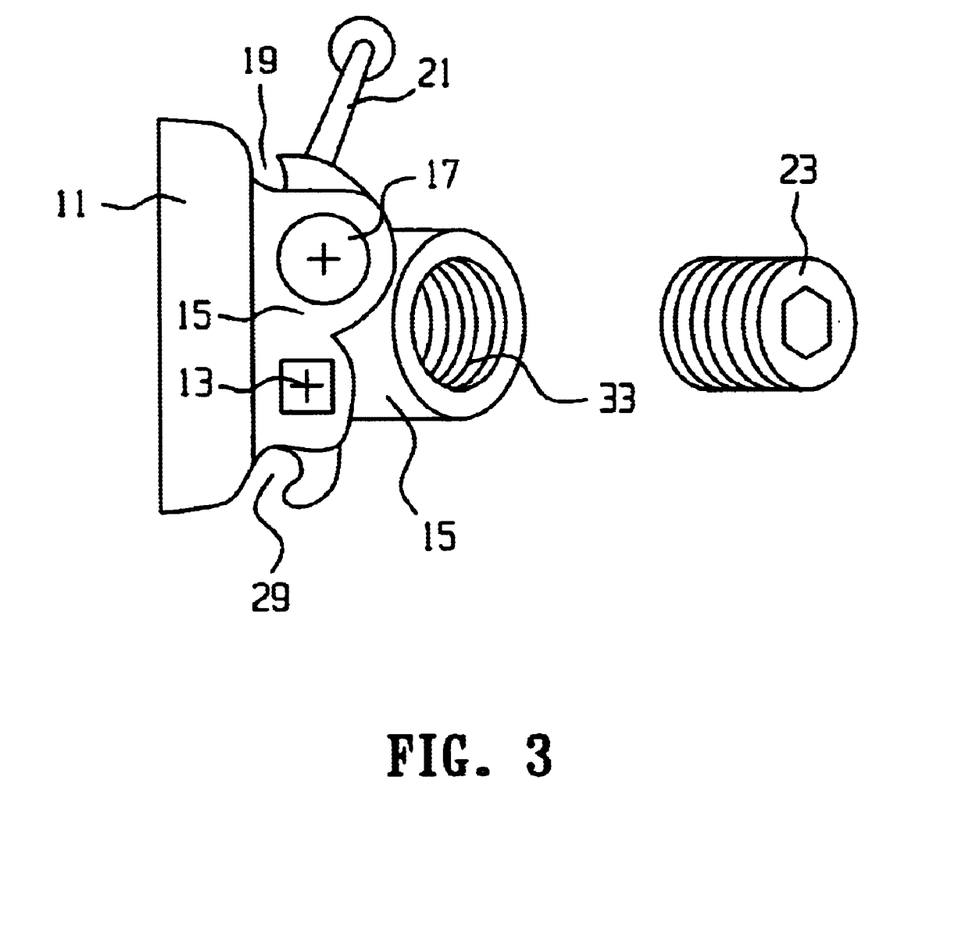
FIG. 3 is an end view of a molar tube according to the invention.

FIG. 3 depicts an end view of a molar tube 10 according to one form of the invention showing the respective dispositions of various elements (essential and non-essential) of the invention, including the base portion 11, body portion 15, lumens 13 and 17, circular channel 29, channel 19, hook arm 21, threaded bore 33, boss 15, and set screw 23.

Figure 4:
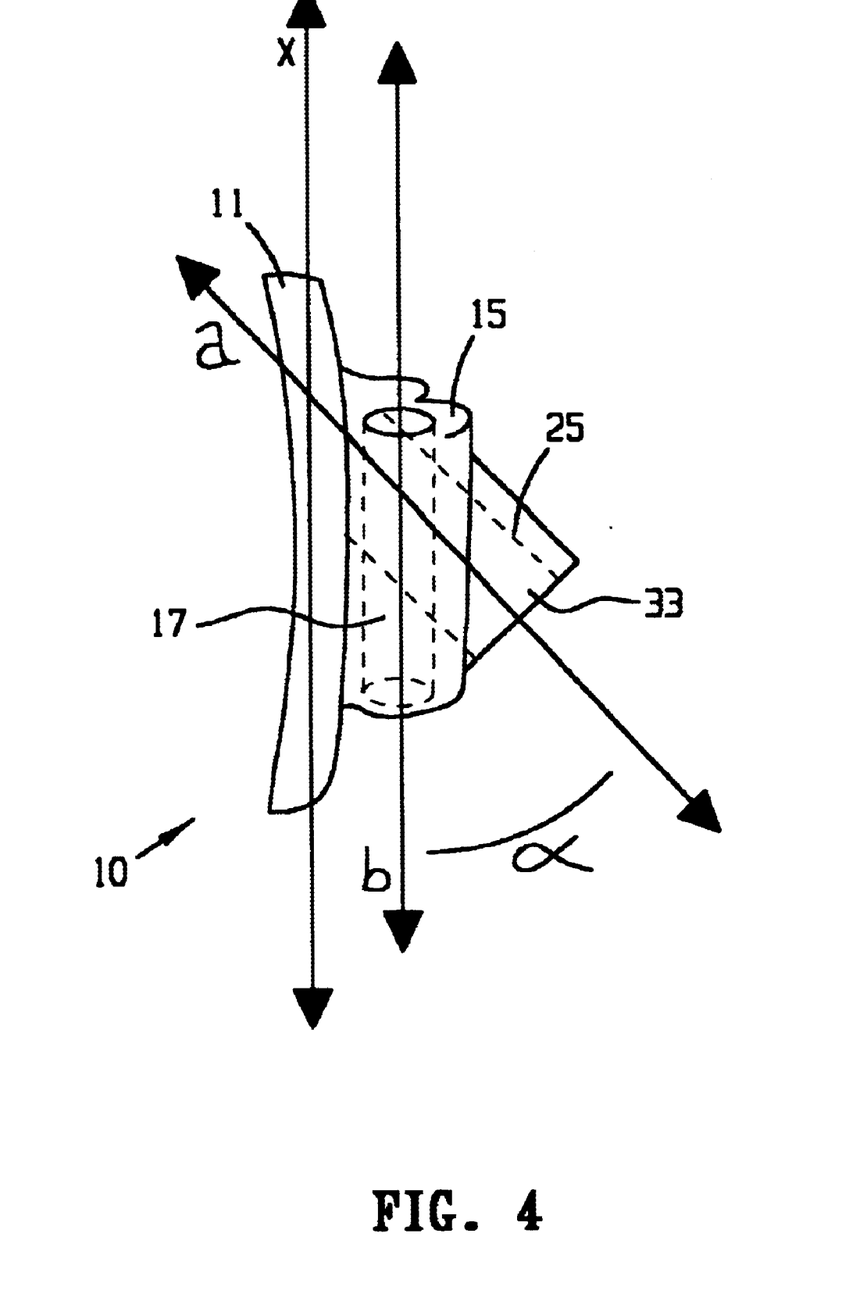
FIG. 4 is a top view of a molar tube according to the invention.

FIG. 4 depicts a top view of a molar tube 10 according to one form of the invention showing the respective dispositions of various elements of the invention, including the base portion 11, body portion 15, boss portion 25 and lumen 17. The threaded bore portion 33 has an axis a, and the lumen 17 has an axis b. There is an angle α, which represents the angle of intersection between the centerlines of the threaded bore portion 33 and the lumen 17, as viewed from the top of the molar tube 10. This angle α may be any angle between about 15 degrees and 175 degrees. More preferably α is any angle in the range of between about 30 degrees and 150 degrees. It is most preferred that α is any angle between 60 degrees and 30 degrees, with an angle α of about 45 degrees being most preferred. There is also shown in FIG. 4 the mesial-distal length dimension x of the base portion 11. Thus, it can be seen that the axis b of the lumen 17 substantially coincides with the mesial-distal length dimension of the base portion 11. For purposes of this invention and the appended claims "substantially coincides" means that the angle of intersection of the axes b and x is +−20 degrees, on either side of their being parallel to one another, and including the case where they are parallel. According to a preferred form of the invention, this angle of intersection is less than 7 degrees; however any degree between 0 and 20 degrees of intersection of these axes is within the scope of the present invention.

Figure 5:
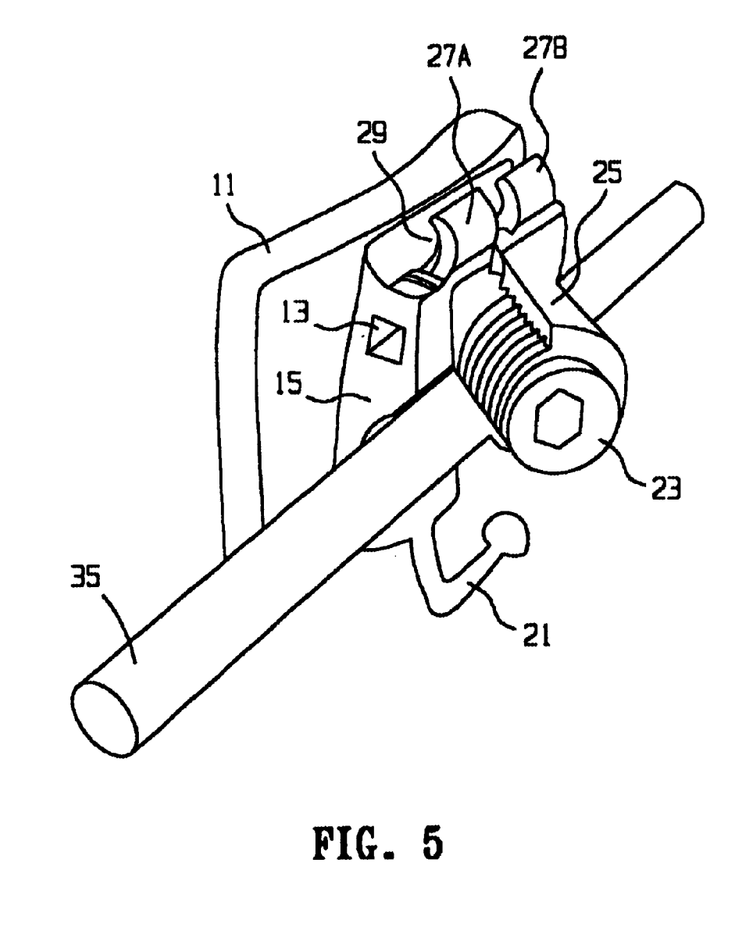
FIG. 5 is a perspective view of a molar tube according to the invention showing a cutaway section.

FIG. 5 depicts a perspective view of a molar tube 10 according to one form of the invention having an archwire 35 of circular cross-section in place within lumen 17 and showing the respective dispositions of various elements (essential and non-essential) of the invention, including setscrew 23, boss portion 25, ears 27a and 27b, circular channel 29, base portion 11, body portion 15, and hook arm 21. A part of the boss portion 25 is cut away to show how the setscrew 23 securedly engages the archwire 35 in position against the inner wall of the lumen in which the archwire is disposed.

Figure 6:
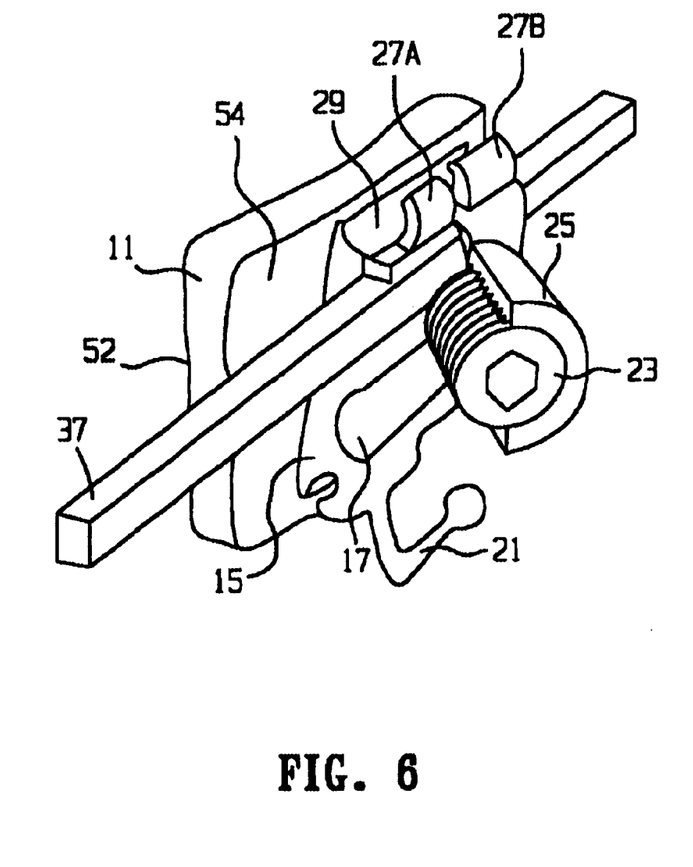
FIG. 6 is a perspective view of a molar tube according to the invention showing a cutaway section.

FIG. 6 depicts a perspective view of a molar tube 10 according to one form of the invention having an archwire 37 of square cross-section in place within lumen 13 and showing the respective dispositions of various elements (essential and non-essential) of the invention, including setscrew 23, boss portion 25, ears 27a and 27b, circular channel 29, base portion 11, body portion 15, and hook arm 21. A part of the boss portion 25 is cut away to show how the setscrew 23 securedly engages the archwire 37 in position against the inner wall of the lumen in which the archwire is disposed.

Figure 7:
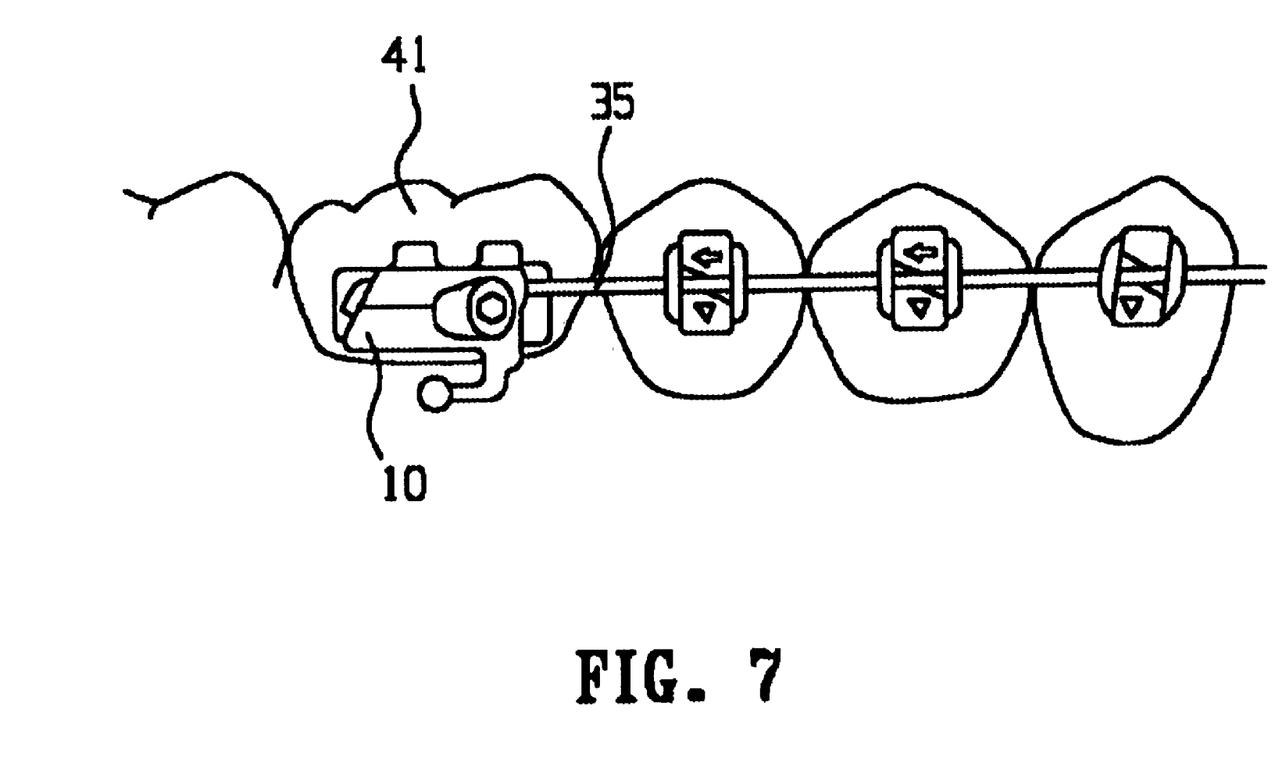
FIG. 7 is a buccal side view of a molar tooth having a molar tube according to the invention affixed thereto.

FIG. 7 is a view from the buccal side perspective of a molar tube 10 according to the invention that is banded or bonded to a molar tooth 41, and also shows archwire 35.

Figure 8:
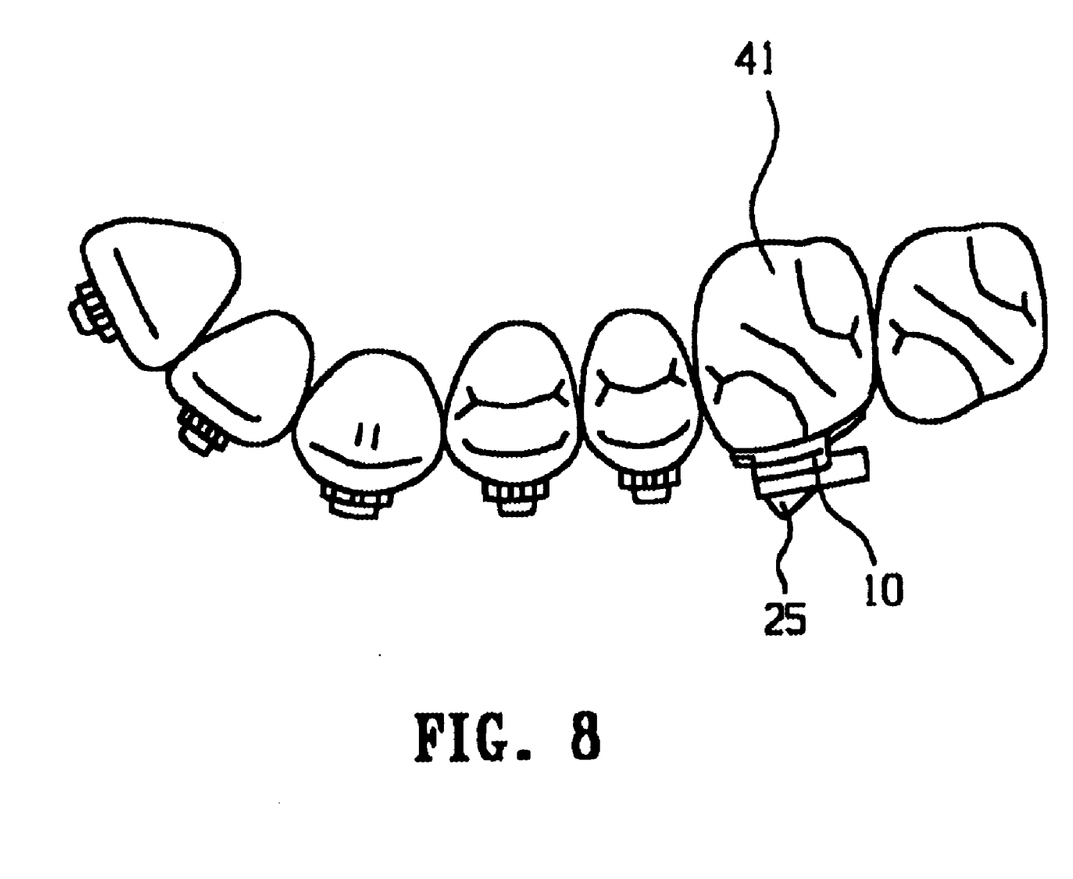
FIG. 8 is a top view of a molar tooth having a molar tube according to the invention affixed thereto.

FIG. 8 is a view from the buccal side perspective of a molar tube 10 according to the invention that is banded or bonded to a molar tooth 41.

Although the base portion 11 and body portion 15 have been described herein as separate elements of a molar tube according to the invention, the present invention contemplates the case where the base portion 11 and body portion 15 are both of the same construction, as in the case of when a molar tube according to the present invention comprises a single casting which includes both base portion 11 and body portion 15.

A molar tube according to the invention may be attached to a band mounted on a molar tooth for the purpose of anchoring the distal end of an archwire, or it may be directly bonded to the tooth itself using bonding agents known in the dental arts for such purposes. The long axis of the molar tube, or the mesial-distally extending axis, is substantially perpendicular to the long axis of the tooth on which it is mounted. It will be appreciated that when a band is used, it may be of any suitable type that is preferably made of stainless steel and suitably cemented to the molar tooth to which a molar tube according to the invention is affixed. However, the molar tube may also be mounted on a bondable base for bonding directly to a tooth. It should also be appreciated that it is preferable to construct the molar tube of stainless steel although any other suitable materials may be used. It will be appreciated by those skilled in this art that the shape of the body portion 15 may be other than as illustrated and also that the molar tube may be a part of an appliance having other elements such as a tube for receiving headgear or a lip bumper and which also may include a suitable hook for connecting elastics to other appliances along the arch. The molar tube lock illustrated in FIG. 1 is for a lower left molar and would likewise be usable on molar tubes designed for use in the other three quadrants, i.e., lower right, upper right, and upper left. Further, it should be appreciated that, as with all such tooth-mounted appliances, the exterior edges are rounded to enhance their comfort in the mouth.

A molar tube of the invention serves to anchor distal ends of an archwire wherein the archwire would be received within the lumen and, depending upon the amount of archwire material protruding from the distal end of the tube, usually trimmed. Next, the setscrew is tightened against the archwire within the lumen in which the archwire is disposed. Preferably, the excess wire protruding from the distal end of the lumen is completely trimmed off by shearing. The securing of the archwire in position using the force applied by the tightening of the setscrew serves to prevent the archwire from moving mesially through the tube during treatment that, if permitted, could lead to opening of spaces between teeth along the arch. This arrangement also helps to prevent the molar from drifting or moving forward (i.e., it acts as an anchor) when so desired.

Importantly, it is not necessary that the set screw be tightened in all cases, i.e., it is sometimes desirable to allow the wire to pass and move freely through the molar tubes. In one sense, a molar tube lock according to the invention can be viewed as an adjunct to achieve selected tooth movements and improve efficiency of orthodontic treatments. There are cases where the main goal is not to secure an archwire in the tube per se because on occasion the wire needs to move freely in the tube (for example., when retracting anterior teeth, or closing spaces in this manner). After some space closure has been achieved, tightening the set screw will secure the arch wire and prevent spaces from re-opening. This can be viewed in many cases as being more advantageous than binding the distal end of the archwire.

While there are many different arrangements and sizes of buccal tubes, buccal tubes (on the facing) are usually welded to a preformed orthodontic band. Then, the band of the attachment is fitted on the tooth according to size and cemented in position. A molar tube lock according to the present invention can be used on a wide variety of molar tube configurations in the manners herein described to provide a lock for an archwire when desired.

Subsequent to the securing of the distal end of the archwire within a lumen of a molar tube according to the invention, it is often necessary to withdraw the wire from the tube. This necessity may occur during any or all of the visits that a patient would periodically make with an orthodontist. It is principally at this time that the molar tube of the present invention becomes advantageous inasmuch as the force required to mesially withdraw the archwire is substantially reduced or entirely eliminated by the present invention. This reduction is obtained by the fact that the only force which holds the archwire in position within the tube is that force exerted by the setscrew, which, when relieved, permits the archwire to be freely withdrawn from the lumen in which it resided, because the wire has been allowed to remain straight.

Although in embodiments of the present invention which include a plurality of lumens 13 and 17 which are adapted to receive archwires of different cross-sectional geometries the axes of the lumens 13 and 17 have heretofore been described as being parallel to one another, or as being generally parallel to the mesial-distally extending axis of a molar tooth to which a molar tube according to the invention is affixed, the present invention also contemplates embodiments in which the contained axes of one or more lumens are disposed at an angle with respect to the mesial-distally extending axis of a molar tooth to which a molar tube according to the invention is to be affixed. By providing an inclined lumen wall, the tooth may be prevented against mesial crown tipping but can be allowed distal crown tipping. Thus, a second feature of the molar tube of the invention is that it may facilitate a desired controlled degree of distal crown tipping.

From the foregoing, it will be appreciated that the molar tube of the present invention increases the well being of the patient by reducing the discomfort associated with the withdrawal of an archwire from a molar tube. Both the magnitude and the duration of the removal force are reduced. Further, the molar tube of the present invention not only reduces archwire withdrawal forces but can also permit distal crown tipping of the molar on which the tube is mounted. In addition, metal fatigue on the wire used is decreased due to there being no necessity to bend the distal ends of the archwire, which in many cases alleviates wire breakage. Arch wire tie backs with ligature wire can also be eliminated.

Consideration must be given to the fact that although this invention has been described and disclosed in relation to certain preferred embodiments, obvious equivalent modifications and alterations thereof will become apparent to one of ordinary skill in this art upon reading and understanding this specification and the claims appended hereto. Accordingly, the presently disclosed invention is intended to cover all such modifications and alterations, and is limited only by the scope of the claims that follow.

I claim:

1. A molar tube useful in orthodontic dentistry comprising:
   a) a base portion having a first face portion that is adapted to be adhered to a molar tooth, a second face portion, and a mesial-distal length dimension; and
   b) a body portion disposed on said second face portion of said base portion, said body portion comprising an upper portion and a lower portion, and wherein said body portion further comprises:
      i) a lumen that is adapted to receive an archwire, wherein said lumen has an axis which substantially coincides with said mesial-distal length dimension of said base portion;
      ii) a boss comprising a threaded bore that is adapted to receive a setscrew, said threaded bore having an axis, wherein said axis of said threaded bore intersects with said mesial-distal length dimension to form an angle of any degree between 35 degrees and 55 degrees, including every degree therebetween.

2. A molar tube according to claim 1 wherein said lumen has a cross section selected from the group consisting of: square, rectangular, or circular.

3. A molar tube according to claim 1 wherein said base portion and said body portion are collectively part of a single casting.

4. A molar tube according to claim 1 wherein said upper portion of said body portion further comprises a channel having a length dimension that coincides with said mesial-distal length dimension of said base portion, and wherein said channel is semi-circular in cross section.

5. A molar tube according to claim 1 wherein said lower portion of said body portion further comprises a channel having a length dimension that coincides with said mesial-distal length dimension of said base portion, and wherein said channel is semi-circular in cross section.

6. A molar tube according to claim 1 wherein said lower portion of said body portion comprises a hook arm, which is useful as an anchor point for elastics.

7. A molar tube according to claim 1 further comprising a setscrew threadedly engaged within said threaded bore.

8. A molar tube according to claim 1 wherein said axis of said threaded bore intersects with said mesial-distal length dimension to form an angle of about 45 degrees.

9. A molar tube useful in orthodontic dentistry composing:
   a) a base portion having a first face portion that is adapted to be adhered to a molar tooth, a second face portion, and a mesial-distal length dimension; and
   b) a body portion disposed on said second face portion of said base portion, said body portion comprising an upper portion and a lower portion, and wherein said body portion further comprises:
      i) a first lumen having an axis which substantially coincides with said mesial-distal length dimension of said base portion;
      ii) a second lumen having an axis which substantially coincides with said mesial-distal length dimension of said base portion;

iii) a boss comprising a threaded bore that is adapted to receive a setscrew, said threaded bore having an axis which is skew to at least one of said axis of said first lumen or said axis of said second lumen; wherein said axis of said threaded bore intersects with said mesial-distal length dimension to form an angle of any degree, between 35 degrees and 55 degrees, including every degree therebetween.

10. A molar tube according to claim 9 wherein said first lumen has a cross section selected from the group consisting of: square, rectangular, or circular.

11. A molar tube according to claim 9 wherein said second lumen has a cross section selected from the group consisting of: square, rectangular, or circular.

12. A molar tube according to claim 9 wherein the cross section of said first lumen is the same as the cross section of said second lumen.

13. A molar tube according to claim 9 wherein the cross section of said first lumen is different from the cross section of said second lumen.

14. A molar tube according to claim 9 wherein the cross section of said first lumen is selected from the group consisting of: square or rectangular; and wherein the cross section of said second lumen is selected from the group consisting of: circular or elliptical.

15. A molar tube according to claim 9 wherein said base portion and said body portion are collectively part of a single casting.

16. A molar tube according to claim 9 wherein said upper portion of said body portion further comprises a channel having a length dimension that coincides with said mesial-distal length dimension of said base portion, and wherein said channel is semi-circular in cross section.

17. A molar tube according to claim 9 wherein said lower portion of said body portion further comprises a channel having a length dimension that coincides with said mesial-distal length dimension of said base portion, and wherein said channel is semi-circular in cross section.

18. A molar tube according to claim 9 wherein said lower portion of said body portion comprises a hook arm, which is useful as an anchor point for elastics.

19. A molar tube according to claim 9 further comprising a setscrew threadedly engaged within said threaded bore.

20. A molar tube according to claim 9 wherein said axis of said threaded bore intersects with said mesial-distal length dimension to form an angle of about 45 degrees.

* * * * *